(12) United States Patent
Rice

(10) Patent No.: US 7,223,898 B2
(45) Date of Patent: May 29, 2007

(54) ISOMERIZATION PROCESS

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/078,504

(22) Filed: Mar. 11, 2005

(65) Prior Publication Data

US 2006/0205990 A1    Sep. 14, 2006

(51) Int. Cl.
*C07C 5/27* (2006.01)
(52) U.S. Cl. ...................... 585/738; 585/734
(58) Field of Classification Search .............. 585/738, 585/734
See application file for complete search history.

(56) References Cited

U.S. PATENT DOCUMENTS

| | | | |
|---|---|---|---|
| 2,966,528 A | 12/1960 | Haensel | 260/666 |
| 3,442,794 A | 5/1969 | Van Helden et al. | 208/111 |
| 3,755,144 A | 8/1973 | Asselin | 208/95 |
| 3,836,597 A | 9/1974 | Sie | 260/683.65 |
| 4,709,116 A | 11/1987 | Zarchy et al. | 585/738 |
| 4,709,117 A | 11/1987 | Gray, Jr. | 585/738 |
| 4,717,784 A | 1/1988 | Stem et al. | 585/738 |
| 4,804,802 A | 2/1989 | Evans et al. | 585/734 |
| 4,831,209 A | 5/1989 | Kruse | 585/738 |
| 5,146,037 A | 9/1992 | Zarchy et al. | 585/738 |
| 5,326,926 A | 7/1994 | Rice | 585/738 |
| 5,705,730 A | 1/1998 | Zarchy et al. | 585/738 |
| 6,706,659 B2 | 3/2004 | Gillespie et al. | 502/217 |
| 7,022,889 B2 * | 4/2006 | Gillespie et al. | 585/750 |

OTHER PUBLICATIONS

Handbook of Petroleum Refining Processes, edited by Robert A. Meyers, published by McGraw-Hill Book Company (1986), pp. 5-49 through 5-51.

* cited by examiner

*Primary Examiner*—Thuan Dinh Dang
(74) *Attorney, Agent, or Firm*—Maryann Maas

(57) ABSTRACT

A process for the isomerization of a feedstream comprising $C_5$–$C_6$ hydrocarbons where the process involves charging hydrogen and a feedstream comprising at least normal $C_5$–$C_6$ hydrocarbons into an isomerization zone and contacting said hydrogen and feedstream with an isomerization catalyst at isomerization conditions to increase the branching of the feedstream hydrocarbons and produce an isomerization effluent stream comprising at least normal pentane, normal hexane, methylbutane, dimethylbutane, and methylpentane has been discovered. Without passing through a stabilizer, the isomerization effluent stream is passed to a deisohexanizer zone to generate at least a stream enriched in methylbutane and dimethylbutanes. The stream enriched in methylbutane and dimethylbutanes is passed to an isomerate striper column to remove butane and lighter hydrocarbons and gasses. The remainder containing the methylbutane and dimethylbutanes is collected for use in, for example, gasoline blending.

20 Claims, 4 Drawing Sheets

ISOMERIZATION PROCESS

FIELD OF THE INVENTION

This invention relates generally to the isomerization of hydrocarbons. This invention relates more specifically to the isomerization of light paraffins using a solid catalyst, and the separation of more highly branched paraffins from less highly branched paraffins by fractionation.

BACKGROUND OF THE INVENTION

High octane gasoline is required for modern gasoline engines. Formerly it was common to accomplish octane number improvement by the use of various lead-containing additives. As lead was phased out of gasoline for environmental reasons, octane ratings were maintained with other aromatic and low vapor pressure hydrocarbons. Environmental damage caused by the vaporization of low vapor pressure hydrocarbons and the health hazards of benzene in motor fuel will lead to further restrictions on octane blending components. Therefore, it has become increasingly necessary to rearrange the structure of the $C_5$ and $C_6$ hydrocarbons used in gasoline blending in order to obtain high octane levels. Catalytic isomerization is a widely used process for this upgrading.

The traditional gasoline blending pool normally includes $C_4$ and heavier hydrocarbons having boiling points of less than 205° C. (395° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. With eventual phase out of lead additives octane improvement was obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branched-chain isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Moreover, the health concerns related to benzene are likely to generate overall restrictions on benzene and possibly aromatics as well, which some view as precursors for benzene tail pipe emissions. Therefore, it is preferred to change the $C_6$ paraffins to an isomerization unit to obtain $C_6$ isoparaffin hydrocarbons. Consequently, octane upgrading commonly uses isomerization to convert $C_6$ and lighter boiling hydrocarbons.

The effluent from an isomerization reaction zone will contain at least a mixture of more highly branched and less highly branched paraffins, hydrogen and light ends containing from one to four carbon atoms. Hydrogen is generally removed in a product separator unit and recycled to the isomerization reactor. Traditionally the light ends are removed from the desired isomerized products in a stabilizer. In order to further increase the octane of the products from the isomerization zone, normal paraffins, and sometimes less highly branched isoparaffins, are typically recycled to the isomerization zone along with the feedstream in order to increase the ratio of less highly branched paraffins to more highly branched paraffins entering the isomerization zone. A variety of methods are known to treat the effluent from the isomerization zone for the recovery of normal paraffins and monomethyl-branched isoparaffins for recycling these less highly branched paraffins to the isomerization zone.

Relatively higher octane isomers are commonly separated from lower octane normal paraffins and monomethyl-branched paraffins by using a distillation zone, adsorptive separation or some combination thereof. General arrangements for the separation and recycling of $C_5$ and $C_6$ hydrocarbons in isomerization units are shown and described at pages 5–49 through 5-51 of THE HANDBOOK OF PETROLEUM REFINING PROCESSES, edited by Robert A. Meyers, published by McGraw-Hill Book Company (1986). Distillation is a primary method of recovering the desired higher octane isomers from the lower octane isomers with the lower octane isomers potentially being recycled to the isomerization zone.

Similarly, another technique for separating the high octane isomers from the lower octane isomers is adsorptive separation under liquid phase conditions. In such methods, the isomerization effluent contacts a solid adsorbent having a selectivity for normal paraffins to effect the selective adsorption of normal paraffins and allow recovery of the isoparaffins as a high octane product. Contacting the normal paraffin containing adsorbent with the desorbent material in a desorption step removes normal paraffins from the adsorbent for recycle to the isomerization zone. Both the isoparaffin and normal paraffin containing streams undergo a separation for the recovery of desorbent before the isoparaffins are recovered as a product and the normal paraffins recycled to the isomerization zone. Liquid phase adsorption has been carried out in conventional swing bed systems as shown in U.S. Pat. No, 2,966,528. The use of simulated moving bed systems for the selective adsorption of normal paraffins is also known and disclosed by U.S. Pat. No. 3,755,144. Simulated moving bed systems have the advantage of increasing recovery and purity of the adsorbed and non-adsorbed components in the isomerization zone effluent for a given unit of adsorbent material.

Adsorption processes using vapor phase adsorption for the separation of normal and branched paraffins are also well known. Examples of such processes are described in U.S. Pat. Nos. 4,709,116 and 4,709,117. These references teach the use of multiple adsorbent vessels and the steps of adsorbing and desorbing the normal paraffins from an isomerization zone effluent. In addition, one or more steps of blowdown or void space purging are also taught to increase the recovery of product hydrocarbons.

Recent efforts in adsorptive separation teach adsorbents and flow schemes for also separating monomethyl paraffins from dimethyl-branched paraffins. U.S. Pat. Nos. 4,717,784 and 4,804,802 disclose processes for the isomerization of a hydrocarbon feed and the use of multiple adsorptive separations to generate normal paraffin and monomethyl-branched paraffin recycle streams. In such systems the effluent from the isomerization zone enters a molecular sieve separation zone that contains a 5 A-type sieve and a ferrierite-type sieve that adsorb normal paraffins and monomethyl-branched paraffins, respectively. U.S. Pat. No. 4,804,802 discloses steam or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

Another method of recovering the high octane isomers from lower octane isomers and normal paraffins uses adsorptive separation followed by distillation. U.S. Pat. No. 3,755, 144 shows a process for the isomerization of a pentane/ hexane feed and the separation of normal paraffins from the isomerization zone effluent. The isomerization zone effluent is separated by a molecular sieve separation zone that includes facilities for the recovery of desorbent from the normal paraffin containing stream that is recycled to the isomerization zone. An extract stream that contains isoparaffins is sent to a deisohexanizer column that separates isopentane and dimethylbutane as a product stream and provides a recycle stream of isohexane that is returned to the isomerization zone.

The present invention involves an isomerization process that eliminates a commonly employed unit. Specifically, the present invention eliminates the need for a stabilizer column to separate the light ends from the desired isomerized products. Stabilizer columns have been traditionally used in isomerization processes, see U.S. Pat. No. 5,146,037, 4,831, 209, 5,705,730 and 5,326,926. In the present invention however, the effluent of the isomerization reactor is passed to a product separator to remove and recycle hydrogen, and then to a separation zone having a deisohexanizer and an isomerate stripper that removes the light ends as well as separates high octane product or gasoline blending from lower octane product for recycle to the isomerization zone. The costly stabilizer column is eliminated and the function of the stabilizer is accomplished by the separation zone of the invention. The present invention provides an isomerization process having lower capital costs and lower utilities costs due to the elimination of the stabilizer column.

SUMMARY OF THE INVENTION

The invention is a process for the isomerization of a feedstream comprising $C_5$–$C_6$ hydrocarbons where the process involves charging hydrogen and a feedstream comprising at least normal $C_5$–$C_6$ hydrocarbons into an isomerization zone and contacting said hydrogen and feedstream with an isomerization catalyst at isomerization conditions to increase the branching of the feedstream hydrocarbons and produce an isomerization effluent stream comprising at least normal pentane, normal hexane, methylbutane, dimethylbutane, and methylpentane. Isomerization catalysts may be zeolitic or chlorided platinum alumina. The isomerization effluent stream to a product separator to separate a hydrogen-rich stream from an isomerized product stream. The isomerized product stream is passed to a deisohexanizer to separate a butane and light ends stream, an isomerate product stream containing higher octane isomers, a recycle stream containing lower octane isomers, and a heavy hydrocarbon stream containing cyclohexane and hydrocarbons having seven or more carbon atoms. The isomerate product stream is conducted to an isomerate stripper column to remove additional butane and light ends.

DETAILED DESCRIPTION OF THE INVENTION

Figure 1:
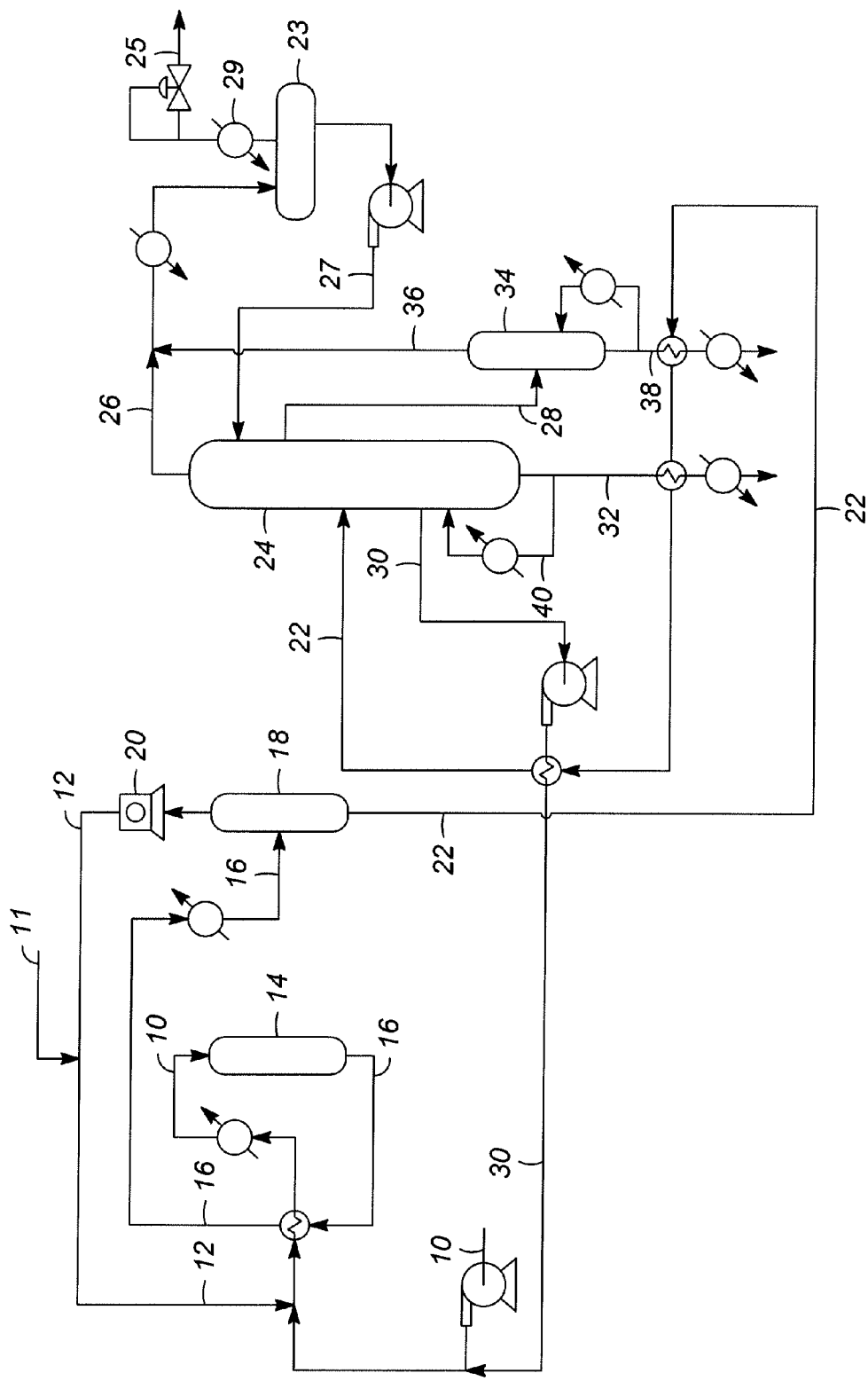
FIG. 1 is a schematic drawing of the process of this invention when employing a zeolitic isomerization catalyst and including the deisohexanizer separation zone. The feed to the isomerate stripper is withdrawn as a side cut stream from the deisohexanizer column and an optional chiller on the condenser overhead stream is shown.

Applicants have discovered that the isomerization of a feedstock containing $C_5$ and $C_6$ hydrocarbons can be successfully achieved in a less costly flowscheme than that currently in use in industry. Specifically, in an isomerization process using a solid catalyst, the traditional stabilizer column may be eliminated and the separation of light ends from isomerized products, usually performed by the stabilizer column instead may be accomplished in the deisohexanizer separation zone. Optionally, lower octane methylpentanes and normal hexane may be recycled to the isomerization zone to increase the octane number. In general, a feedstock comprising $C_5$–$C_6$ hydrocarbons is contacted with an isomerization catalyst in an isomerization zone at isomerization conditions and thereby increases the branching of the feedstream hydrocarbons and produces an isomerization zone effluent stream that comprises at least hydrogen, normal pentane, normal hexane, methylbutane, dimethylbutane and methylpentane, and light ends. The effluent from the isomerization zone passes first to a product separator to remove and optionally recycle hydrogen. The bottoms of the product separator which contains the isomerized products and light ends are conducted to a separation zone. The light ends, a recycle stream, a $C_7^+$ stream and an isomerized product stream are all separated in the separation zone.

The feedstocks that can be used in this invention include hydrocarbon fractions rich in $C_4$–$C_6$ normal paraffins. The term "rich" is defined to mean a stream having more than 50% of the mentioned components. One category of feedstocks are substantially pure normal paraffin streams having from 4 to 6 carbon atoms or a mixture of such substantially pure normal paraffins. Other useful feedstocks include light natural gasoline, light straight run naphtha, gas oil condensate, light raffinates, light reformate, light hydrocarbons, field butanes, and straight run distillates having distillation end points of about 77° C. (170° F.) and containing substantial quantities of $C_4$–$C_6$ paraffins. The feed stream may also contain low concentrations of unsaturated hydrocarbons and hydrocarbons having more than 6 carbon atoms.

Hydrogen is admixed with the feed in an amount that will provide a hydrogen to hydrocarbon ratio equal to or less than 0.05 in the effluent from the isomerization zone when operating without hydrogen recycle. The hydrogen to hydrocarbon ratio of 0.05 or less at the effluent has been found to provide sufficient excess hydrogen for operation of the process. Although no net hydrogen is consumed in the isomerization reaction, the isomerization zone will have a net consumption of hydrogen often referred to as the stoichiometric hydrogen requirement which is associated with a number of side reactions that occur. These side reactions include cracking and disproportionation. Other reactors that will also consume hydrogen include olefin and aromatics saturation. For feeds having a low level of unsaturates, satisfying the stoichiometric hydrogen requirements demand a hydrogen to hydrocarbon molar ratio for the outlet stream of between 0.01 to 10.0. Hydrogen in excess of the stoichiometric amounts for the side reactions is maintained in the reaction zone to provide good stability and conversion by compensating for variations in feed stream compositions that alter the stoichiometric hydrogen requirements.

When the hydrogen to hydrocarbon ratio exceeds 0.10, it is not economically desirable to operate the isomerization process without the recycle of hydrogen to the isomerization zone. As the quantity of hydrogen leaving the product recovery section increases, additional amounts of $C_4$ and other product hydrocarbons are taken by the fuel gas stream from the product recovery section. The value of the lost product or the additional expense associated with recovery facilities to prevent the loss of product do not justify operating the process without recycle at hydrogen to hydrocarbon ratios above 0.10. However, when employing hydrogen recycle, hydrogen is admixed with the feed in an amount that will provide a hydrogen to hydrocarbon ratio equal to from 0.01 to about 10.0 in the effluent from the isomerization zone Hydrogen may be added to the feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in the outlet stream or one of the outlet stream fractions is monitored by a hydrogen monitor and the control valve setting position is adjusted to maintain the desired hydrogen concentration. The hydrogen concentration at the effluent is calculated on the basis of total effluent flow rates.

The effluent or extract from the adsorption section is contacted in the isomerization zone with an isomerization catalyst. The catalyst composites that can be used in the isomerization zone include traditional isomerization catalysts including chlorided platinum alumina, crystalline aluminosilicates or zeolites, and other solid strong acid catalysts such as sulfated zirconia and modified sulfated zirconia. Suitable catalyst compositions of this type will exhibit selective and substantial isomerization activity under the operating conditions of the process.

As a class, the crystalline aluminosilicate or crystalline zeolite catalysts comprise crystalline zeolitic molecular sieves having an apparent pore diameter large enough to adsorb neopentane. A silica alumina molar ratio $SiO_2:Al_2O_3$ of greater than 3; less than 60 and preferably between 15 and 30 is desirable. In one form, the zeolite will contain an equivalent percentage of alkali metal cations and will have those $AlO_4$-tetrahedra not associated with alkali metal cations, either not associated with any metal cations or associated with divalent or other polyvalent metal cations. Usually the molecular sieve is a mordenite molecular sieve, which is essentially in the acid form or is converted to the acid form. Catalysts of this type for isomerization are disclosed in detail in U.S. Pat. Nos. 3,442,794 and 3,836,597.

A composition of zeolitic catalyst for use in the present invention comprises a Group VIII noble metal, a hydrogen form crystalline aluminosilicate, and a refractory inorganic oxide with the catalyst composition having a surface area of at least 580 m$^2$/g. Significant improvements in isomerization performance are realized when the surface area of the catalytic composite is at or above 580 m$^2$/g. A Group VIII metal is incorporated into the catalytic composite to supply a hydrogenation/dehydrogenation function and a particular Group VIII noble metal is platinum. The Group VIII noble metal is present in an amount from about 0.01 to 5% by weight of the composite and preferably in an amount of at least 0.15% by weight but not over 0.35% by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are one embodiment, particularly with a silica to alumina ratio of at least 16:1. The hydrogen form aluminosilicate may be present in an amount within the range of 50 to about 99.5 wt-%, preferably within the range of 75 to about 95 wt-%, and a refractory inorganic oxide may be present in an amount within the range of from 25 to about 50 wt-%.

Another suitable isomerization catalyst is a solid strong acid catalyst which comprises a sulfated support of an oxide or hydroxide of a Group IVB (IUPAC 4) metal, preferably zirconium oxide or hydroxide, at least a first component which is a lanthanide element or yttrium component, and at least a second component being a platinum-group metal component. The catalyst optionally contains an inorganic-oxide binder, especially alumina. The catalyst is fully described in U.S. Pat. No. 6,706,659 which is hereby incorporated by reference in its entirety.

The support material of the solid strong acid catalyst comprises an oxide or hydroxide of a Group IVB (IUPAC 4). In one embodiment the Group IVB element is zirconium or titanium. Sulfate is composited on the support material. A component of a lanthanide-series element is incorporated into the composite by any suitable means. The lanthanide series element component may be selected from the group consisting of lanthanum, cerium, praseodymium, neodymium, promethium, samarium, europium, gadolinium, terbium, dysprosium, holmium, erbium, thulium, ytterbium and lutetium. Suitable amounts of the lanthanide series element component are in the range of about 0.01 to about 10 mass-% on an elemental basis, of the catalyst. A platinum-group metal component is added to the catalytic composite by any means known in the art to effect the catalyst of the invention, e.g., by impregnation. The platinum-group metal component may be selected from the group consisting of platinum, palladium, ruthenium, rhodium, iridium, or osmium. Amounts in the range of from about 0.01 to about 2 wt-% platinum-group metal component, on an elemental basis are suitable.

Optionally, the catalyst is bound with a refractory inorganic oxide. The binder, when employed, usually comprises from about 0.1 to 50 mass-%, preferably from about 5 to 20 mass-%, of the finished catalyst. The support, sulfate, metal components and optional binder may be composited in any order effective to prepare a catalyst useful for the isomerization of hydrocarbons. Examples of suitable atomic ratios of lanthanide or yttrium to platinum-group metal for this catalyst is at least about 1:1; about 2:1 or greater; and about 5:1 or greater. The catalyst may optionally further include a third component of iron, cobalt, nickel, rhenium or mixtures thereof. For example, iron may be present in amounts ranging from about 0.1 to about 5 wt-% on an elemental basis. Production of the catalyst is described in U.S. Pat. No. 6,706,659 B1 which is incorporated by reference in its entirety and not reproduced here. In one embodiment of the invention the solid strong acid isomerization catalyst is sulfated zirconia or a modified sulfated zirconia.

Another class of suitable isomerization catalysts for this invention is the chlorided platinum alumina catalysts. The aluminum is preferably an anhydrous gamma-alumina with a high degree of purity. The catalyst may also contain other platinum group metals. The term "platinum group metals" refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt-% of the platinum. Other platinum group metals may be present in a concentration of from 0.1 to 0.25 wt-%. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 wt-% based upon the dry support material. The use of chloride in amounts greater than 5 wt-% have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

Operating conditions within the isomerization zone are selected to maximize the production of isoalkane product from the feed components. Temperatures within the reaction zone will usually range from about 40° to about 235° C. (100° to 455° F.). Lower reaction temperatures usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60° to 160° C. are suitable. Thus, when the feed mixture contains significant portions of $C_4$–$C_6$ alkanes most suitable operating temperatures are in the range from 145° to 225° C. The reaction zone may be maintained over a wide range of pressures. Pressure conditions in the isomerization of $C_4$–$C_6$ paraffins range from 700 KPaa to 7000 KPaa. In other embodiments pressures for this process are in the range of from 20 barsg to 30 barsg. The feed rate to the reaction zone can also vary over a wide range. These conditions include liquid hourly space velocities ranging from 0.5 to 12 $hr^{-1}$ however, with some embodiments having space velocities between 1 and 6 $hr^{-1}$.

The effluent of the isomerization is processed to separate the desired isomerized products from hydrogen, light ends, lower octane isomerized products, and cyclohexane plus heavy hydrocarbons having 7 or more carbon atoms. The flowscheme does not require a stabilizer column to separate the light ends from the isomerized products. The specifics of different embodiments of the invention are discussed below in reference to the figures.

One embodiment of the invention is described with reference to FIG. 1. Reference to the specific arrangement for this invention is not meant to limit it to the details disclosed therein. Furthermore, FIG. 1 is a schematic illustration and does not show a number of details for the process arrangement such as pumps, compressors, valves, and recycle lines which are well known to those skilled in the art.

FIG. 1 shows three primary operating zones, an isomerization zone, a product separator zone, and a fractionation separation zone. Fresh feed of the type previously described is introduced via line 10 to the isomerization zone 14 which contains zeolitic isomerization catalyst. The isomerization zone is operated at conditions previously discussed. Hydrogen in line 12 is admixed with the feed to the isomerization zone in an amount that will provide a hydrogen to hydrocarbon molar ratio of from 0.01 to 10.0 in the effluent from the isomerization zone. If necessary, make-up gas can be provided through line 11.

The isomerization zone 14 is shown as a single reactor system. The invention is not restricted to a particular type of isomerization zone. The isomerization zone can consist of any type of isomerization zone that takes a stream of $C_5$–$C_6$ straight-chain hydrocarbons or a mixture of straight-chain and branched-chain hydrocarbons and converts straight-chain hydrocarbons in the feed mixture to branched-chain hydrocarbons and branched hydrocarbons to more highly branched hydrocarbons thereby producing an effluent having branched-chain and straight-chain hydrocarbons. A two-reactor system with a first stage reactor and a second stage reactor in the reaction zone is an alternative embodiment. For a two reactor system, the catalyst used is distributed between the two reactors in any reasonable distribution. It is not necessary that the reaction be carried out in two reactors but the use of two reactors confer several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in the first vessel with the rest of the reaction carried out in a final reactor stage at more favorable temperature conditions. For example, the relatively cold hydrogen and hydrocarbon feed mixtures are passed through a cold feed exchanger that heats the incoming feed against the effluent from the final reactor. The feed from the cold feed exchanger is carried to the hot feed exchanger where the feed is heated against the effluent carried from the first reactor. The partially heated feed from hot feed exchanger is carried through an inlet exchanger that supplies any additional heat requirements for the feed and then into a first reactor. Effluent from the first reactor is carried to the second reactor after passage through an exchanger to provide inter-stage cooling. The isomerization zone effluent is carried from second reactor through the cold feed exchanger as previously described and into the separation facilities.

The effluent from the isomerization zone 16 enters a product separator 18 that divides the reaction zone effluent into a product stream 22 comprising $C_4$ and heavier hydrocarbons, and an overhead gas stream 12 which is made up of hydrogen and lighter hydrocarbons including $C_3$ and lighter boiling compounds. The effluent in line 16 may be heat exchanged with the feed stream 10 before being passed to product separator 18. Conditions for the operation of the product separator include pressures ranging from 689 to 4137 KPaa (100 to 600 psia). Specific embodiments utilize pressures from 1379 to 3447 KPaa (200 to about 500 psia). Suitable designs for rectification columns and separator vessels suitable for use as the product separator are well known to those skilled in the art. The product separator may optionally include a preheat loop from which the $C_4^+$ products stream is withdrawn (not shown). The hydrogen-rich gas stream is carried in line 12 from the product separator and is recycled using recycle compressor 20 to combine with feedstock in line 10. Additional hydrogen, if necessary, may be added through line 11. The products stream 22 may be heat exchanged with other streams as shown in FIG. 1 before being passed to deisohexanizer column of the separation zone.

Traditionally, a stabilizer would be employed to remove light gases and butane from the products stream. In the present invention however, products stream 22 is directed to a deisohexanizer column 24. The deisohexanizer column normally runs at a pressure of from 138 to 1379 KPaa (20 to 200 psia) preferably 345 to 689 KPaa (50 to 100 psia). Deisohexanizer column 24 serves a variety of purposes. It provides an overhead stream 26 that contains light gasses and butane. In the operation of a fractionation zone having the arrangement of deisohexanizer 24, the cut point for the overhead stream 26 is above the boiling point of 2,3-dimethylbutane and below the boiling point of butane. 2,3-Dimethylbutane has the higher octane of the dimethylbutane isomers and butane is considered to be too light for gasoline blending. As a result, a good split between overhead stream 26 and upper-sidecut stream 28 is desired to maximize octane and minimize the amount of light material. The amount of butane taken off from the deisohexanizer column will vary depending upon the amount of butane entering the process.

The overhead stream may be recovered for further processing or fuel gas use. The overhead stream may be passed to overhead condenser 23 to generate an offgas stream 25 containing primarily light gasses and butane and recycle stream 27 containing $C_5^+$ hydrocarbons. Recycle stream 27 is conducted to deisohexanizer column 24. Since some $C_5^+$ hydrocarbons may be carried to overhead condenser 23, optional chiller 29 may be placed on the condenser overhead stream 25 in order to minimize loss of $C_5^+$ hydrocarbons.

Figure 2:
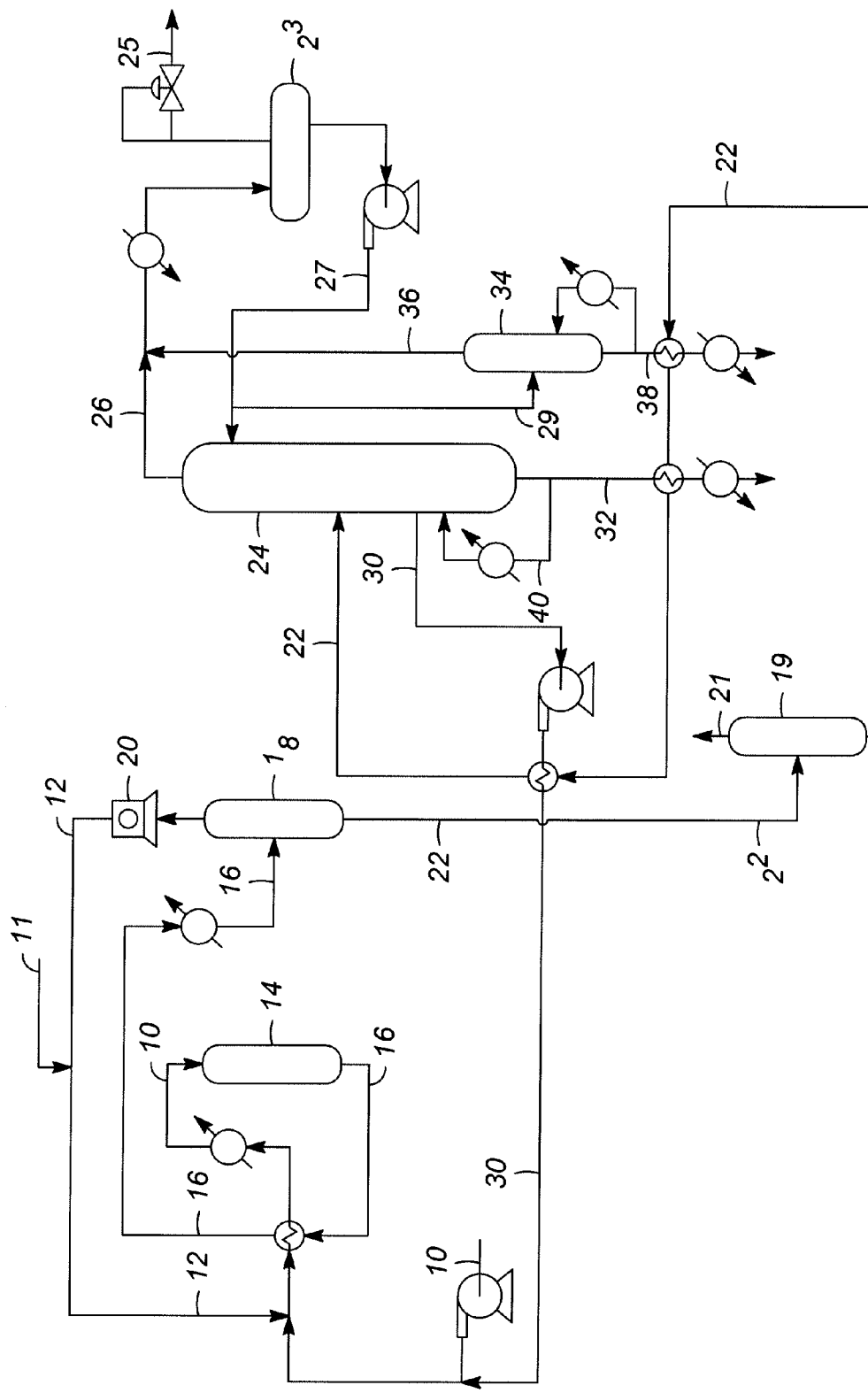
FIG. 2 is a schematic drawing of the process of this invention when employing a zeolitic isomerization catalyst and including the deisohexanizer separation zone. The feed to the isomerate stripper is a portion of the recycle stream from the overhead condenser to the deisohexanizer.

Another choice for minimizing the loss of $C_5^+$ hydrocarbons into condenser overhead stream 25 is shown in FIG. 2 and employs an optional flash drum 19 positioned between product separator 18 and deisohexanizer column 24. Products stream from the product separator in line 22 is introduced into flash drum 19 where hydrogen and other gasses are removed in flash drum overhead stream 21. The remainder of stream 22 is conducted to deisohexanizer column 24. Although it is possible, generally either chiller 29 or flash drum 19 would be employed but not both.

Returning to FIG. 1, deisohexanizer column 24 also provides a product upper-sidecut stream 28 that contains a high concentration of normal pentane, methylbutane and dimethylbutanes and a lower-sidecut $C_6$ recycle stream 30 that comprises normal hexane and monomethylpentanes. Upper-side cut stream 28 may also contain butane and light gasses. The relatively higher octane hydrocarbons, normal pentane, methylbutane and dimethylbutanes, in upper-side cut stream 28 can be recovered from the deisohexanizer column 24 in any manner. Preferably the upper-sidecut stream 28 exits as a sidecut from a single deisohexanizer column 24. In the operation of a fractionation zone having the arrangement of deisohexanizer 24, the cut point for the upper-sidecut stream 28 is above the boiling point of 2,3-dimethylbutane and below the boiling point of 2-methylpentane. 2,3-Dimethylbutane has the higher octane of the dimethylbutane isomers and 2-methylpentane has a relatively low octane number, lower than 3-methylpentane. As a result, a good split between the lower-sidecut 30 and the upper-sidecut stream 28 is desired to maximize octane. Since only a narrow boiling point difference separates 2,3-dimethylbutane and 2-methylpentane, the deisohexanizer is designed to maximize this separation.

Optionally, instead of upper-side cut stream 28, a portion of stream 27 may be directed to isomerate stripper 34 as shown in FIG. 2. Without upper-side cut stream 28, the normal pentane, methylbutane and dimethylbutanes are removed in overhead stream 26 and passed to overhead condenser 23. The normal pentane, methylbutane and dimethylbutanes are removed from overhead condenser 23 in recycle stream 27. Recycle stream 27 is divided into two portions, one portion 29 is conducted to isomerate stripper 34 and the remainder is conducted to deisohexanizer column 24.

Returning to FIG. 1, the relatively lower octane hydrocarbons, normal hexane and monomethylpentanes, can be recovered from the deisohexanizer zone 24 in any manner. Preferably the $C_6$ recycle stream exits as lower sidecut stream 30 from a single deisohexanizer column 24. In the operation of a fractionation zone having the arrangement of deisohexanizer 24, the cut point for lower sidecut stream 30 is below the boiling point of 2,3-dimethylbutane and above the boiling point of 2-methylpentane. 2,3-Dimethylbutane has the higher octane of the dimethylbutane isomers and 2-methylpentane has a relatively low octane number, lower than 3-methylpentane. As a result, a good split between the lower-sidecut stream 30 and upper-sidecut stream 28 is desired to maximize octane. Since only a narrow boiling point difference separates 2,3-dimethylbutane and 2-methylpentane, the deisohexanizer is designed to maximize this separation.

The cut point for lower side-cut stream 30 in deisohexanizer zone 24 is particularly important to the operation of this process. It should be set to recycle essentially all of the methylpentane and normal hexane to the isomerization zone 16. Preferably, deisohexanizer zone 24 will operate with a cut point set at about the boiling point of cyclohexane. With a cyclohexane cut point a substantial portion of cyclohexane and all methylcyclopentane will be recycled to the isomerization zone.

Heavier hydrocarbons are withdrawn from the deisohexanizer column as a heavy hydrocarbon stream 32. For the single column deisohexanizer 24, this heavy hydrocarbon stream is withdrawn by a line 32. Where a full boiling range naphtha is used as the feed to the process, the heavy hydrocarbon feed will comprise a $C_7^+$ naphtha. This bottoms stream will ordinarily be used as the feed in a reforming zone. A cyclohexane cut point between the lower-sidecut and heavy hydrocarbon stream introduce substantial portions of any cyclohexane into the heavy hydrocarbon stream. Such an operation will maximize the production of aromatics from a downstream reforming zone.

The upper-sidecut stream 28 containing normal pentane, methylbutane and dimethylbutanes is passed to an isomerate stripper column 34 to remove light ends. In isomerate stripper column 34 the light ends including butane and light gasses are separated into isomerate stripper overhead 36 which may be combined with deisohexanizer column overhead stream 26. The most desired isomerized products, normal pentane, methylbutane and dimethylbutanes are removed from the isomerate stripper in isomerate product stream 38. Isomerate product stream may be collected or used in gasoline blending. The isomerate stripper column 34 normally runs at a pressure of from 138 to 1379 Kpaa (20 to 200 psia) or 345 to 689 KPaa (50 to 100 psia).

Figure 3:
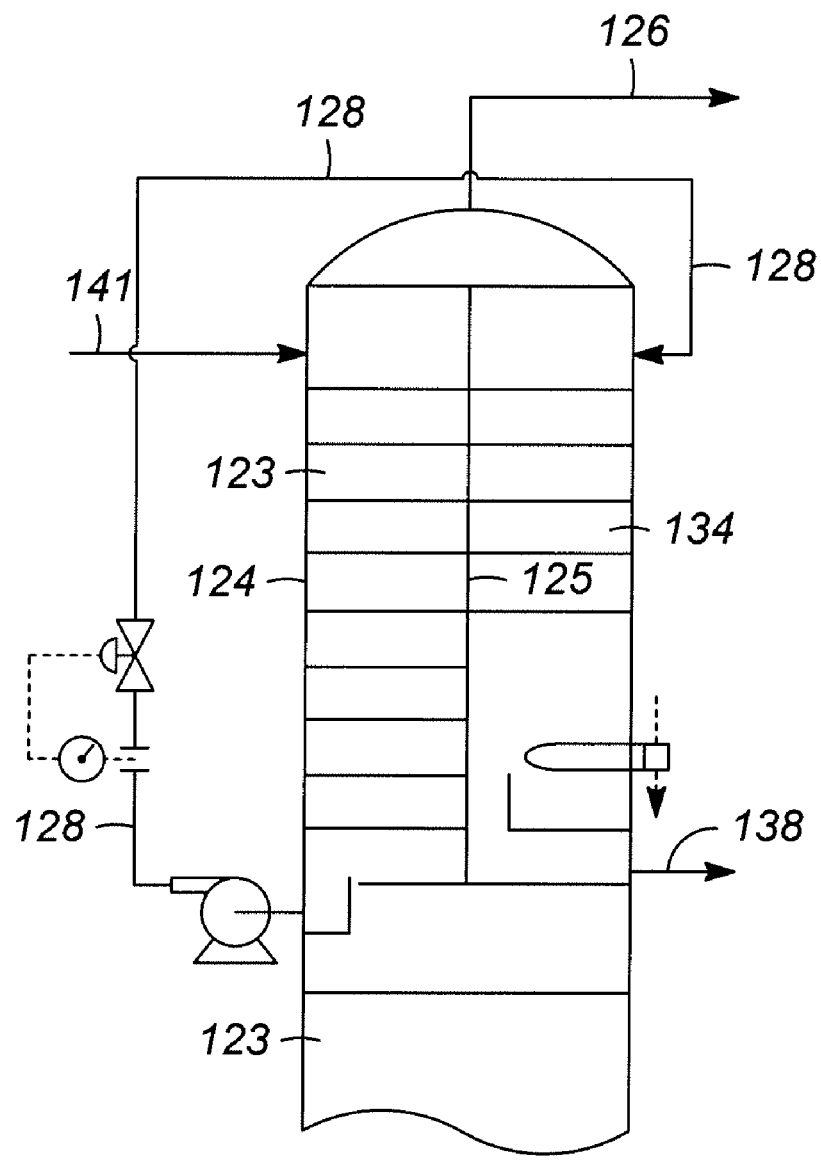
FIG. 3 is a schematic drawing of a portion of one embodiment of the deisohexanizer separation zone

FIG. 3 shows another embodiment where isomerate stripper column and the deisohexanizer column are combined through using a partition so that the isomerate stripper performs as a column within a column. Referring to FIG. 3, column 124 is provided with a substantially fluid tight partition 125 which defines zone 134. Zone 134 operates as a column within a column. The partition forms two parallel fractionation zones within column 124. Zone 134 is defined by the partition and the balance of the volume of column 124 will be referred to as zone 123. The partition is not necessarily centered in the column and the two fractionation zones may differ in cross sectional area or shape. The two zones are isolated from each other for the height of this wall, but communicate at the top end of the column. There is no direct vapor or liquid flow between the two fractionation zones through the partition, but the upper end of zone 134 is open to the internal volume of the column, zone 123. Liquid or vapor may not pass under the partition at the bottom of zone 134. Thus, vapor and liquid can freely move around the partition between the two portions of the column only at the upper ends of zones 123 and 134. Zones 123 and 134 may each be equipped with an independent reboiler. In FIG. 3, reboiler 139 is shown for zone 134.

The effluent of the product separation zone contains light gasses, butane, 2,3-dimethylbutane, 2,2-dimethylbutane, isopentane, 2-methylpentane, 3-methylpentane, methylcyclopentane, cyclohexane and $C_7^+$. For ease of discussion, the product separation zone effluent components will be grouped according to boiling point, which is the main factor in determining their behavior in column 124. The components having the lowest boiling points will be labeled A and will consisting of light gasses and butane. The components having relatively low boiling points will be labeled Group B and will consist of 2,3-dimethylbutane, 2,2-dimethylbutane, and isopentane. Group B contains high-octane components which are desired products of the overall isomerization process. The mid-range boiling components will be labeled Group C and contains 2-methylpentane and 3-methylpentane. Group C contains lower octane components that may be recycled to the isomerization zone and not included in a final product. Group C components may be used for other purposes such as in desorbing normal alkanes in a pressure swing adsorption zone. Separating and recycling the 2-methylpentane and 3-methylpentane results in the final product having a higher overall octane value. The components having relatively high boiling points will be labeled Group D and will consist of methylcyclopentane, cyclohexane, and $C_7^+$. Group D may also contains high-octane components and are desired products of the overall isomerization process. Optionally, the stream containing Group A and the stream containing Group D may be combined to form the final high-octane isomerization process product.

The effluent from the product separation zone is introduced into the combined deisohexanizer and isomerate stripper column 124 at a point below partition 125. The Group A components, Group B components along with a portion of the Group C components present in the product separation zone effluent are driven upward in zone 123. The less volatile Group D components are concentrated into a bottoms liquid that is removed from column 124 (as shown in FIG. 1 line 32). This separation is effected through the use of a reboiler (as shown in FIG. 1 reboiler 40) providing vapor to the bottom undivided fractionation zone. The Group D-rich bottoms liquid may be removed or may be combined with the Group B rich stream from zone 134 to form the overall isomerization process high-octane product. The Group C components are withdrawn from zone 123 in a lower-sidecut stream (as shown in FIG. 1, line 30). The Group C components may be recycled to the isomerization zone for isomerization into components having a higher octane value.

An upper-sidecut stream 128 is withdrawn from zone 123 and passed to zone 134. Upper-sidecut sidecut stream 128 contains the desired isomerized products, Group C. Within zone 134, the desired products are separated from light gasses and butane which are withdrawn in overhead line 126. The methylbutane and dimethylbutane-enriched stream is withdrawn in line 138.

The top of the column is a purification zone which is designed to separate the Group A components from the Group B components. The Group A-enriched stream is removed from the top of the column in overhead line 126 and passed through an overhead condenser (not shown) to form liquid delivered to the receiver. A liquid phase stream of Group A and Group B components is removed from the receiver and divided into a first portion which is returned to the top of the dividing wall fractionation column as reflux line 141 and a second portion which is removed from the process. As used herein the term "rich" or "enriched" is intended to mean that a concentration of the indicated compound, mixture of compounds or class of compounds is greater than 50 and preferably greater than 75 mol-%.

Figure 4:
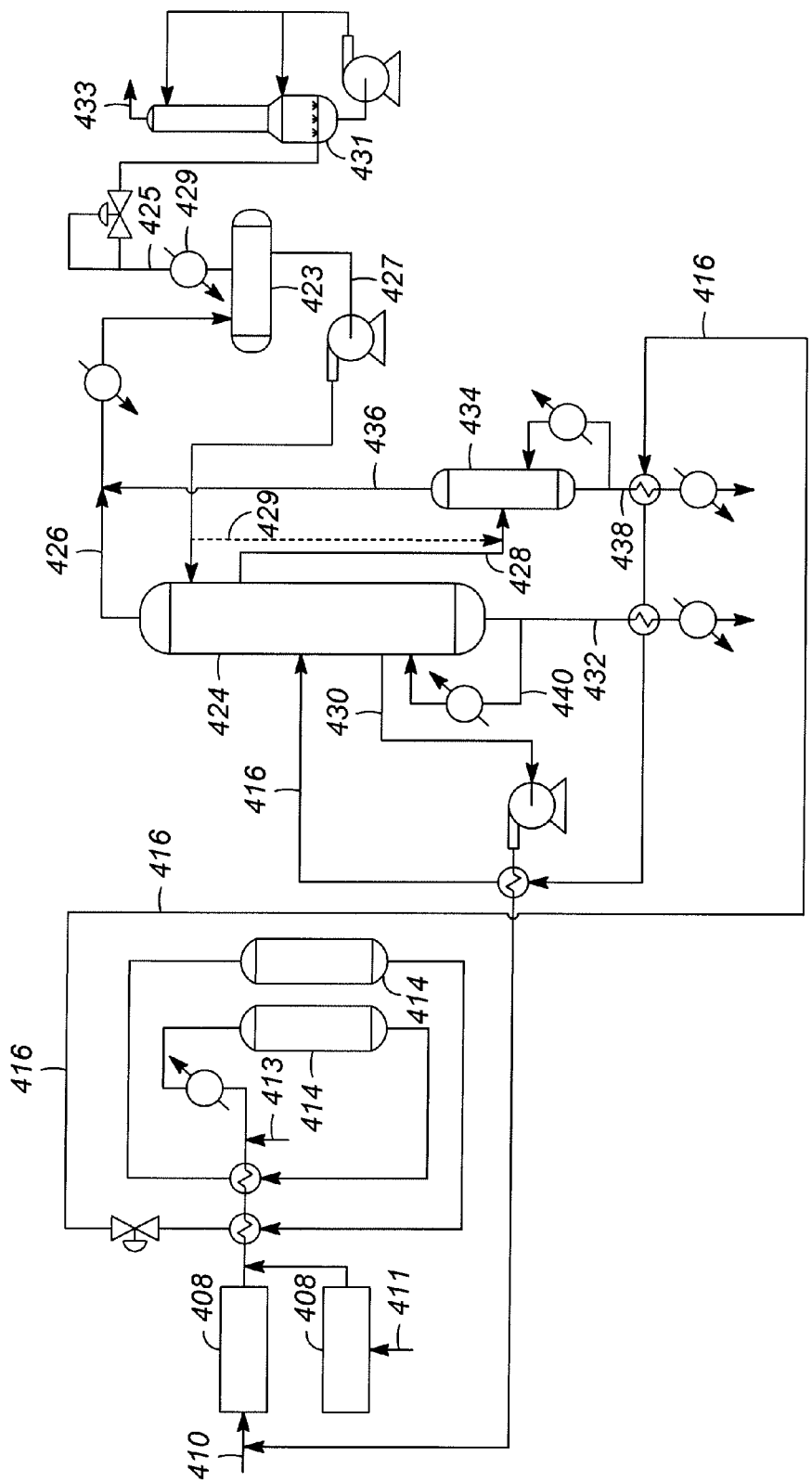
FIG. 4 is a schematic drawing of the process of this invention when employing a chlorided platinum alumina catalyst isomerization catalyst and including the deisohexanizer separation zone.

FIG. 4 shows yet another embodiment of the invention. FIG. 4 shows three primary operating zones, an isomerization zone, a product separator zone, and a fractionation separation zone. Fresh feed of the type previously described is passed through a dryer 408 which is filled with molecular sieve to remove water and is introduced via line 410 to isomerization zone 414 which contains chlorided platinum alumina isomerization catalyst. Hydrogen in line 411 is passed through a dryer 408 which is filled with molecular sieve to remove water and is introduced to isomerization zone 414. Isomerization zone 414 is operated at conditions previously discussed. Hydrogen in line 411 is admixed with the feed to the isomerization zone in an amount that will provide a hydrogen to hydrocarbon molar ratio of from 0.01 to 10.0 in the effluent from the isomerization zone.

Since operation of the reaction zone with the chlorided platinum alumina catalyst also requires the presence of a small amount of an organic chloride promoter, an organic chloride is injected into feed stream 410 via chloride injection line 413. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. One example of a promoter compound is carbon tetrachloride. Other suitable promoter compounds include oxygen-free decomposable organic chlorides such as propyldichloride, butylchloride, and chloroform. The need to keep the reactants dry is reinforced by the presence of the organic chloride compound which converts to hydrogen chloride. As long as the process streams are kept dry, there will be no adverse effect from the presence of hydrogen chloride.

The isomerization zone 414 is shown as a two reactor system with a first stage reactor and a second stage reactor. Details of the two-reactor system are as described above. The invention is not restricted to a particular type of isomerization zone. The isomerization zone can consist of any type of isomerization zone that takes a stream of $C_5$–$C_6$ straight-chain hydrocarbons or a mixture of straight-chain and branched-chain hydrocarbons and converts straight-chain hydrocarbons in the feed mixture to branched-chain hydrocarbons and branched hydrocarbons to more highly branched hydrocarbons thereby producing an effluent having branched-chain and straight-chain hydrocarbons.

The effluent from the isomerization zone 416 is passed to a separation zone containing deisohexanizer column 424. The isomerization zone effluent 416 may be heat exchanged with other streams as shown in FIG. 4 before being passed to deisohexanizer column 424 of the separation zone. There is no need for a product separation zone since there is no hydrogen recycle. Traditionally, a stabilizer would be employed prior to the deisohexanizer column 424 to remove light gases, such as hydrogen chloride, and butane from the isomerization effluent stream 416. In the present invention however, isomerization effluent stream 416 is directed to deisohexanizer column 424 without employing a stabilizer.

Deisohexanizer column 424 is operated at conditions discussed above, and with the resulting four separated streams as discussed above. The overhead stream 426 contains light gasses, such as hydrogen chloride, and butane and after scrubbing, may be recovered for further processing or fuel gas use. The overhead stream may be passed to overhead condenser 423 to generate an offgas stream 425 containing primarily light gasses and butane and recycle stream 427 containing $C_5^+$ hydrocarbons. Recycle stream 427 is conducted to deisohexanizer column 424. Offgas stream 425 is passed to caustic gas scrubber 431 to remove any chloride resulting in chloride free offgas in line 433. Since some $C_5^+$ hydrocarbons may be carried to overhead condenser 423, optional chiller 429 may be placed on the condenser overhead stream 425 in order to minimize loss of $C_5^+$ hydrocarbons.

Another choice for minimizing the loss of $C_5^+$ hydrocarbons into condenser overhead stream 25 is to incorporate an optional flash drum (not shown) positioned between isomerization zone 414 and deisohexanizer column 424. Isomerization zone effluent in line 416 is introduced into a flash drum where hydrogen and other gasses are removed in a flash drum overhead stream. The remainder of stream 414 is conducted to deisohexanizer column 424. Although it is possible, generally either chiller 429 or a flash drum would be employed but not both.

Deisohexanizer column 424 also provides a product upper-sidecut stream 428 that contains a high concentration of normal pentane, methylbutane and dimethylbutanes and a lower-sidecut $C_6$ recycle stream 430 that comprises normal hexane and monomethylpentanes. Upper-side cut stream 428 may also contain butane and light gasses. The relatively higher octane hydrocarbons, normal pentane, methylbutane and dimethylbutanes, in upper-side cut stream 428 can be recovered from the deisohexanizer column 424 in any manner. Preferably the upper-sidecut stream 428 exits as a sidecut from a single deisohexanizer column 424. The upper sidecut stream 428 is achieved as described earlier in reference to FIG. 1.

The relatively lower octane hydrocarbons, normal hexane and monomethylpentanes, can be recovered from the deisohexanizer zone 424 in any manner and are recycled to the isomerization zone. Preferably the $C_6$ recycle stream exits as lower sidecut stream 430 from a single deisohexanizer column 424. The lower sidecut stream 430 is achieved as described earlier in reference to FIG. 1.

Heavier hydrocarbons are withdrawn from the deisohexanizer column as a heavy hydrocarbon stream 432. For the single column deisohexanizer 424, this heavy hydrocarbon stream is withdrawn by a line 432. Where a full boiling range naphtha is used as the feed to the process, the heavy hydrocarbon feed will comprise a $C_7^+$ naphtha. This bottoms stream will ordinarily be used as the feed in a reforming zone. A cyclohexane cut point between the lower-sidecut and heavy hydrocarbon stream introduce substantial portions of any cyclohexane into the heavy hydrocarbon stream. Such an operation will maximize the production of aromatics from a downstream reforming zone.

The upper-sidecut stream 428 containing normal pentane, methylbutane and dimethylbutanes is passed to an isomerate stripper column 434 to remove light ends. In isomerate stripper column 434 the light ends including butane and light gasses are separated into isomerate stripper overhead 436 which may be combined with deisohexanizer column overhead stream 426. The most desired isomerized products, normal pentane, methylbutane and dimethylbutanes are removed from the isomerate stripper in isomerate product stream 438. Isomerate product stream may be collected or used in gasoline blending. The isomerate stripper column 434 normally runs at a pressure of from 138 to 1379 Kpaa (20 to 200 psia) or 345 to 689 KPaa (50 to 100 psia).

Optionally, instead of upper-side cut stream 428, a portion of stream 427 may be directed to isomerate stripper 434 as shown by dotted line 429. Without upper-side cut stream 428, the normal pentane, methylbutane and dimethylbutanes are removed in overhead stream 426 and passed to overhead condenser 423. The normal pentane, methylbutane and dimethylbutanes are removed from overhead condenser 423 in recycle stream 427. Recycle stream 427 is divided into two portions, one portion 429 is conducted to isomerate stripper 434 and the remainder is conducted to deisohexanizer column 424.

The embodiment shown in FIG. 3 where isomerate stripper column and the deisohexanizer column are combined through using a partition so that the isomerate stripper performs as a column within a column may be used wherein the catalyst is chlorided platinum alumina, such as in FIG. 4, as well as wherein the catalyst is zeolitic, such as in FIGS. 1 and 2. The above description of FIG. 3 is applicable to the embodiment of the invention using the chlorided platinum alumina catalyst and where isomerate stripper column and the deisohexanizer column are combined through using a partition so that the isomerate stripper performs as a column within a column.

The effluent of the isomerization zone 414 in line 416 contains light gasses, butane, 2,3-dimethylbutane, 2,2-dimethylbutane, isopentane, 2-methylpentane, 3-methylpentane, methylcyclopentane, cyclohexane and $C_7^+$. As above, and for purposes of discussion, the product separation zone effluent components are grouped according to boiling point, which is the main factor in determining their behavior in column 124. The components having the lowest boiling points are labeled A and comprise of light gasses and butane. The components having relatively low boiling points are labeled Group B and comprise of 2,3-dimethylbutane, 2,2-dimethylbutane, and isopentane. Group B contains high-octane components which are desired products of the overall isomerization process. The mid-range boiling components are labeled Group C and comprise 2-methylpentane and 3-methylpentane. Group C contains lower octane components that may be recycled to the isomerization zone and not included in a final product. Group C components may be used for other purposes such as in desorbing normal alkanes in a pressure swing adsorption zone. Separating and recycling the 2-methylpentane and 3-methylpentane results in the final product having a higher overall octane value. The components having relatively high boiling points are labeled Group D and comprise methylcyclopentane, cyclohexane, and $C_7^+$. Group D may also contains high-octane components and are desired products of the overall isomerization process. Optionally, the stream containing Group A and the stream containing Group D may be combined to form the final high-octane isomerization process product.

Viewing FIGS. 3 and 4, the combined column 124 of FIG. 3 replaces the two-column system, columns 424 and 434 of FIG. 4. Specifically, the effluent from the isomerization zone 414 is conducted via line 416 and introduced into the combined deisohexanizer and isomerate stripper column 124 at a point below partition 125. The Group A components, Group B components along with a portion of the Group C components present in the product separation zone effluent are driven upward in zone 123. The less volatile Group D components are concentrated into a bottoms liquid that is removed from column 124 (as shown in FIG. 4 line 432). This separation is effected through the use of a reboiler (as shown in FIG. 4 reboiler 440) providing vapor to the bottom undivided fractionation zone. The Group D-rich bottoms liquid may be removed or may be combined with the Group B rich stream from zone 134 to form the overall isomerization process high-octane product. The Group C components are withdrawn from zone 123 in a lower-sidecut stream (as shown in FIG. 4, line 430). The Group C components may be recycled to the isomerization zone for isomerization into components having a higher octane value.

An upper-sidecut stream 128 is withdrawn from zone 123 and passed to zone 134. Upper-sidecut sidecut stream 128 contains the desired isomerized products, Group C. Within zone 134, the desired products are separated from light gasses and butane which are withdrawn in overhead line 126. The methylbutane and dimethylbutane-enriched stream is withdrawn in line 138.

The top of the column is a purification zone which is designed to separate the Group A components from the Group B components. The Group A-enriched stream is removed from the top of the column in overhead line 126 and passed through an overhead condenser (not shown) to form liquid delivered to the receiver. A liquid phase stream of Group A and Group B components is removed from the receiver and divided into a first portion which is returned to the top of the dividing wall fractionation column as reflux line 141 and a second portion which is removed from the process.

What is claimed is:

1. A process for the isomerization of a feedstream comprising $C_5$–$C_6$ hydrocarbons said process comprising:
    charging hydrogen and a feedstream comprising at least normal $C_5$–$C_6$ hydrocarbons into an isomerization zone and contacting said hydrogen and feedstream with an isomerization catalyst at isomerization conditions to increase the branching of the feedstream hydrocarbons and produce an isomerization effluent stream comprising at least butane, normal pentane, normal hexane, methylbutane, dimethylbutanes, methylpentanes and hydrocarbons having seven or more carbon atoms;
    passing the isomerization zone effluent to a deisohexanizer zone to separate four streams, a deisohexanizer zone overhead stream comprising at least butane, a first deisohexanizer zone sidecut stream comprising at least methylbutane and dimethylbutanes, a second deisohexanizer zone sidecut stream comprising at least methylpentanes and normal hexane, and a deisohexanizer zone bottoms stream comprising at least hydrocarbons having seven or more carbon atoms; and
    passing the first deisohexanizer zone sidecut stream to an isomerate stripper zone to separate an isomerate stripper zone overhead stream comprising at least butane from an isomerate stripper zone product stream containing methylbutane and dimethylbutanes.

2. The process of claim 1 further comprising passing the isomerization zone effluent through a product separator zone to separate a product separator zone overhead stream containing hydrogen from the isomerization effluent stream before passing the isomerization zone effluent to the deisohexanizer zone and recycling the product separator zone overhead stream to the isomerization zone.

3. The process of claim 1 wherein the isomerate stripper zone is defined by a partition within the deisohexanizer zone and performs as a column within a column.

4. The process of claim 1 further comprising recycling the second deisohexanizer zone sidecut stream to the isomerization zone.

5. The process of claim 1 wherein the isomerization zone effluent stream enters the deisohexanizer zone through an intermediate column elevation through a first inlet point and the first deisohexanizer zone sidecut stream is withdrawn at a point located above the first inlet point and the second deisohexanizer zone sidecut stream is withdrawn at a point located below the first inlet point.

6. The process of claim 1 wherein said isomerate stripper zone product stream is blended into a gasoline pool to produce a motor fuel.

7. The process of claim 1 wherein the catalyst is a chlorided platinum alumina catalyst.

8. The process of claim 1 further comprising passing the isomerization zone effluent through a flash drum to separate a flash drum overhead stream containing butane and lighter boiling hydrocarbons and gasses from the isomerization effluent stream before passing the isomerization zone effluent to the deisohexanizer zone.

9. The process of claim 1 further comprising passing the deisohexanizer zone overhead stream to a receiver to separate a receiver bottoms stream comprising C5 and higher boiling hydrocarbons from a receiver overhead stream comprising C4 and lower boiling hydrocarbons wherein the receiver overhead stream is cooled to minimize the amount of C5 and higher boiling hydrocarbons.

10. The process of claim 1 wherein said reaction zone includes a series of two reactors, the feed stream first enters a reactor operating at a temperature in the range of 120° to 225° C. and said effluent is recovered from a reactor operating at a temperature in the range of 60° to 160° C.

11. A process for the isomerization of a feedstream comprising $C_5$–$C_6$ hydrocarbons said process comprising:
    charging hydrogen and a feedstream comprising at least normal $C_5$–$C_6$ hydrocarbons into an isomerization zone and contacting said hydrogen and feedstream with an isomerization catalyst at isomerization conditions to increase the branching of the feedstream hydrocarbons and produce an isomerization effluent stream comprising at least hydrogen, butane, normal pentane, normal hexane, methylbutane, dimethylbutanes, methylpentanes and hydrocarbons having seven or more carbon atoms;
    passing the isomerization effluent stream to a product separator zone to separate a product separator zone overhead stream containing hydrogen from a product separator zone effluent containing the remainder of the isomerization effluent stream;
    passing the product separator zone effluent to a deisohexanizer zone to separate four streams, a deisohexanizer zone overhead stream comprising at least butane, a first deisohexanizer zone sidecut stream comprising at least methylbutane and dimethylbutanes, a second deisohexanizer zone sidecut stream comprising at least methylpentanes and normal hexane, and a deisohexanizer zone bottoms stream comprising at least hydrocarbons having seven or more carbon atoms; and
    passing the first deisohexanizer zone sidecut stream to an isomerate stripper zone to separate an isomerate stripper zone overhead stream comprising at least butane from an isomerate stripper zone product stream containing methylbutane and dimethylbutanes.

12. The process of claim 11 wherein the isomerate stripper zone is defined by a partition within the deisohexanizer zone and performs as a column within a column.

13. The process of claim 11 further comprising recycling the second deisohexanizer zone sidecut stream and the product separator overhead stream to the isomerization zone.

14. The process of claim 11 wherein the product separator zone effluent stream enters the deisohexanizer through an intermediate column elevation through a first inlet point and the first deisohexanizer zone sidecut stream is withdrawn at a point located above the first inlet point and the second deisohexanizer zone sidecut stream is withdrawn at a point located below the first inlet point.

15. The process of claim 11 wherein said an isomerate stripper zone product stream is blended into a gasoline pool to produce a motor fuel.

16. The process of claim 11 wherein the catalyst is a solid strong acid catalyst or a zeolite.

17. The process of claim 11 further comprising combining the deisohexanizer zone overhead stream and the isomerate stripper zone overhead stream into a single stream.

18. The process of claim 11 further comprising passing the product separator zone effluent through a flash drum to separate a flash drum overhead stream containing butane and lighter boiling hydrocarbons and gasses from the isomerization effluent stream before passing the product separator zone effluent to the deisohexanizer zone.

19. The process of claim 11 further comprising passing the deisohexanizer zone overhead stream to a receiver to separate a receiver bottoms stream comprising C5 and higher boiling hydrocarbons from a receiver overhead stream comprising C4 and lower boiling hydrocarbons wherein the receiver overhead stream is cooled to minimize the amount of C5 and higher boiling hydrocarbons.

20. The process of claim 11 wherein said reaction zone includes a series of two reactors, the feed stream first enters a reactor operating at a temperature in the range of 120° to 225° C. and said effluent is recovered from a reactor operating at a temperature in the range of 60° to 160° C.

* * * * *